United States Patent
Lieberman

(10) Patent No.: US 7,316,689 B2
(45) Date of Patent: Jan. 8, 2008

(54) APPARATUS FOR DEPOSITING BONE GRAFTING MATERIAL

(75) Inventor: Isador H. Lieberman, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 629 days.

(21) Appl. No.: 10/828,942

(22) Filed: Apr. 21, 2004

(65) Prior Publication Data

US 2004/0215201 A1   Oct. 28, 2004

Related U.S. Application Data

(60) Provisional application No. 60/464,880, filed on Apr. 23, 2003.

(51) Int. Cl.
*A61B 17/58* (2006.01)
(52) U.S. Cl. .................................................. 606/93
(58) Field of Classification Search ............ 606/92–94
See application file for complete search history.

(56) References Cited

U.S. PATENT DOCUMENTS

| | | | |
|---|---|---|---|
| 4,994,065 A | | 2/1991 | Gibbs et al. |
| 5,638,997 A | * | 6/1997 | Hawkins et al. ............. 222/391 |
| 6,367,962 B1 | * | 4/2002 | Mizutani et al. ............. 366/189 |
| 6,582,446 B1 | | 6/2003 | Marchosky |
| 6,599,293 B2 | * | 7/2003 | Tague et al. .................. 606/94 |
| 2002/0092871 A1 | | 7/2002 | Rickard et al. |
| 2003/0036762 A1 | | 2/2003 | Kerr et al. |
| 2004/0024409 A1 | | 2/2004 | Sand et al. |
| 2004/0030345 A1 | | 2/2004 | Aurin et al. |

FOREIGN PATENT DOCUMENTS

| | | |
|---|---|---|
| DE | 201 18 100 U1 | 2/2003 |
| FR | 2 690 332 A1 | 10/1993 |
| FR | 2 829 690 A1 | 3/2003 |
| JP | 07 313586 | 12/1995 |

* cited by examiner

*Primary Examiner*—Eduardo C Robert
*Assistant Examiner*—Michael J. Araj
(74) *Attorney, Agent, or Firm*—Tarolli, Sundheim Covell & Tummino LLP

(57) ABSTRACT

An apparatus for depositing bone graft material into a mammalian body comprises a barrel member having an inner surface with internal threads. The barrel includes an exit port through which bone graft material placed into the barrel exits the barrel. A plunger member is disposed coaxially within the barrel member for pushing the bone graft material toward the exit port in the barrel. A mechanism is provided for advancing the plunger member within the barrel member. The plunger member can be rotatable and include external threads that are complimentary to and engaged with the internal threads in the barrel member to assist in moving the bone graft material toward the exit port in the barrel.

5 Claims, 2 Drawing Sheets

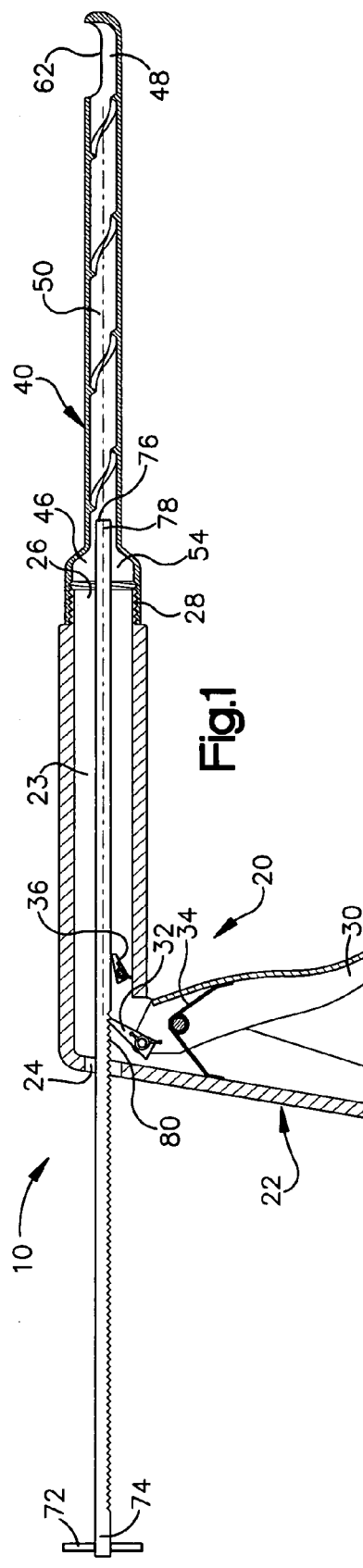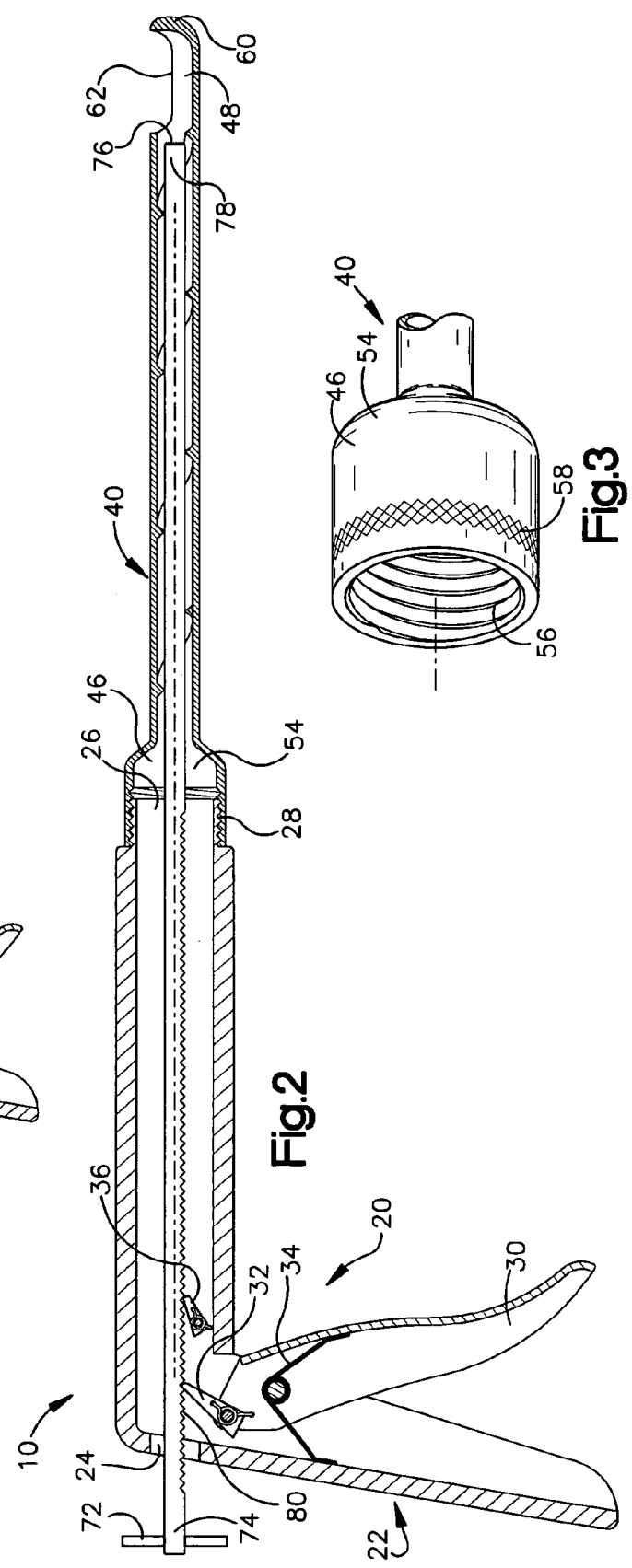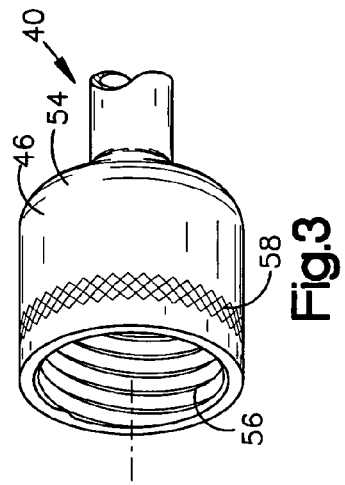

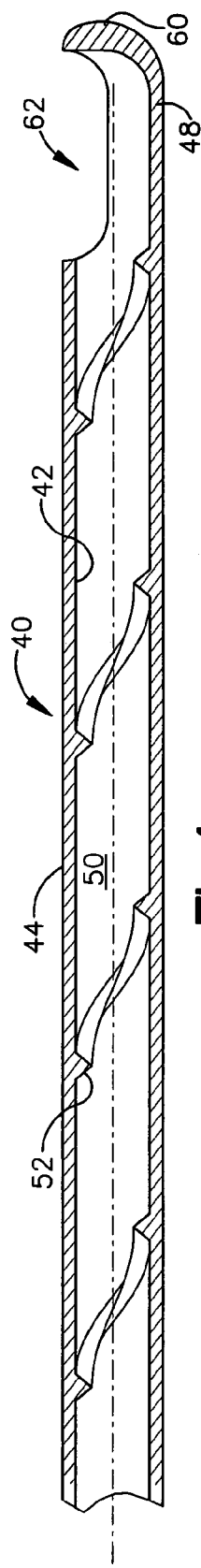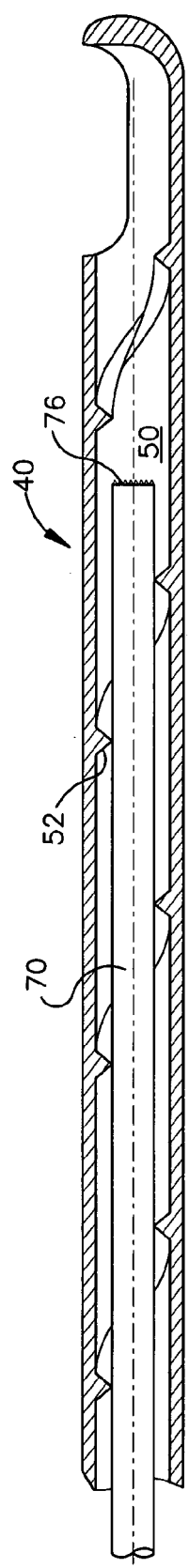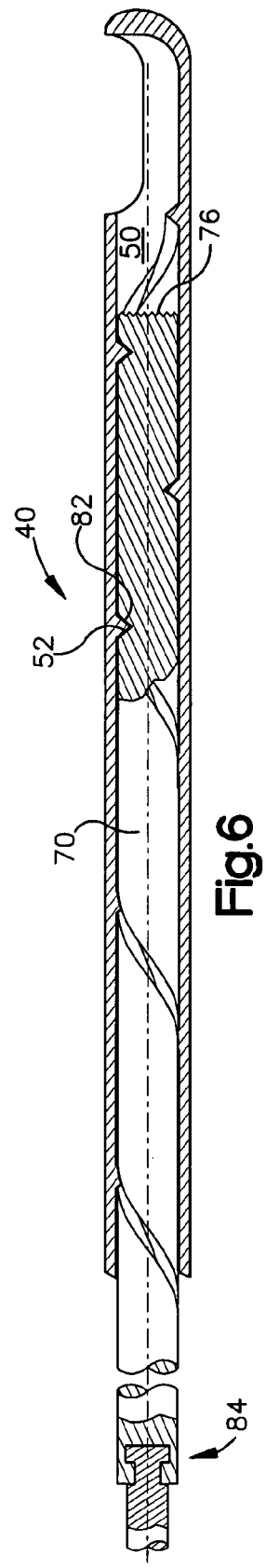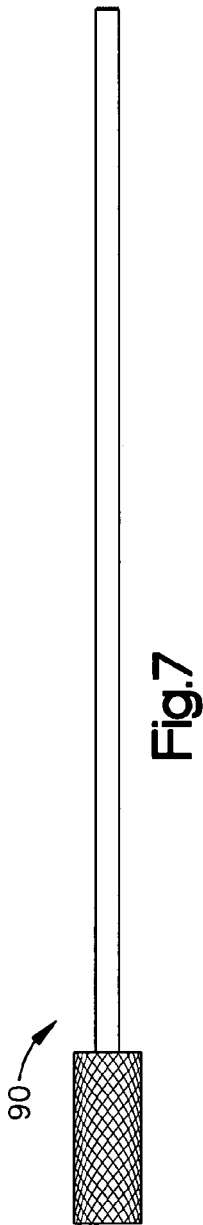

APPARATUS FOR DEPOSITING BONE GRAFTING MATERIAL

RELATED APPLICATION

This application claims priority from U.S. provisional patent application Ser. No. 60/464,880, filed on Apr. 23, 2003, the subject matter of which is incorporated herein by reference.

TECHNICAL FIELD

The present invention relates to an apparatus for depositing bone grafting material into a location in a mammalian body.

BACKGROUND OF THE INVENTION

In the U.S. alone, 250,000 spinal fusion operations are performed annually. The typical spinal fusion procedure includes placing harvested bone graft material and/or a bone substitute material into an intervertebral disc space between adjacent vertebrae to facilitate fusion of the vertebrae.

With increasing experience and technical advancements in minimally invasive spine surgery, the surgeon is faced with constraints in his ability to adequately and efficiently deposit bone graft and/or composite bone substitute into the intervertebral disc space. Spinal fusion surgery can be performed through various exposures and corridors (i.e., anterior lumbar interbody fusion, post-lumbar interbody fusion, endoscopic trans-thoracic or lumbar fusion, posterior lateral or retroperitoneal/trans-sous split). Each of these fusion techniques requires manual packing of bone into the intervertebral disc space which is tedious and time consuming.

A limiting constraint for the surgeon is the size of the opening into the intervertebral disc space to be filled. Another constraint is the distance from the spine that needs to be traversed through percutaneous or portal techniques.

In most of the spinal fusion procedures, a plunger-style device is used to inject the bone graft material into the intervertebral space. Due to the nature of some types of bone graft material, it is common for the plunger to become jammed by some of the bone graft particles. Thus, an apparatus for depositing bone graft material that is designed to prevent jamming is desirable.

SUMMARY OF THE INVENTION

The present invention is an apparatus for depositing bone graft material into a mammalian body. The apparatus comprises a barrel member having an inner surface with internal threads. The barrel includes an exit port through which bone graft material placed into the barrel exits the barrel. A plunger member is disposed coaxially within the barrel member for pushing the bone graft material toward the exit port in the barrel. Means is provided for advancing the plunger member within the barrel member.

In accordance with one aspect of the invention, the plunger member is rotatable and includes external threads that are complimentary to and engaged with the internal threads in the barrel member to assist in moving the bone graft material toward the exit port in the barrel.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a schematic side view of an apparatus for depositing bone graft material into a mammalian body in accordance with the present invention;

FIG. 2 is a view similar to FIG. 1 showing components of the apparatus in different positions;

FIG. 3 is a schematic side view of another portion of the component of the apparatus shown in FIG. 2;

FIG. 4 is a sectional view of a portion of a component of the apparatus of FIG. 1;

FIG. 5 is a sectional view similar to FIG. 4 and includes another component of the invention;

FIG. 6 is a sectional view similar to FIG. 5 and illustrates a second embodiment of the invention;

FIG. 7 is a schematic side view of a loading tool for use with the apparatus of FIG. 1.

DESCRIPTION OF EMBODIMENTS

The present invention relates to an apparatus for depositing bone grafting material into a location in a mammalian body. As representative of the present invention, FIG. 1 illustrates an apparatus 10 comprising a handle assembly 20, a barrel member 40, and a plunger member 7

The handle assembly 20 includes an L-shaped base member 22 with a passage 23 extending through the base member. The base member 22 includes a first opening 24 into the passage 23 at one end of the base member and a second opening 26 into the passage at the other end of the base member. The outer surface of the base member 22 surrounding the second opening 26 includes external threads 28. A manually movable lever 30 is pivotably attached to the base member 22. The lever 30 includes a row of teeth 32. The lever 30 is biased by a spring 34. A lock pawl 36 is attached to the base member 22 inside the passage 22.

The barrel member 40 includes cylindrical inner and outer surfaces 42 and 44 (FIG. 2) that extend between first and second end portions 46 and 48 (FIG. 1). The inner surface 42 defines a bore 50 through the barrel member 40 and includes helical threads 52. The first end portion 46 of the barrel member 40 has an enlarged diameter funnel section 54. The funnel section 54 includes internal threads 56 (FIG. 3) for mating with the threads 28 on the base member 20. The funnel section 54 can also include a knurled outer surface portion 58. The second end portion 48 of the barrel member 40 includes a dull, curved terminal end 60 (FIG. 2) and a radially extending exit port 62 adjacent the terminal end.

The plunger member 70 (FIG. 1) is a rod with a radially extending flange 72 at a first end 74 and scored teeth 76 at a second end 78. Adjacent the first end 74, the plunger member 70 includes rack teeth 80 that engage the teeth 32 on the lever 30.

In accordance with one embodiment of the invention, the outer surface of the plunger member 70 is smooth (FIGS. 2 and 5) and has an outer diameter that is less than the maximum inner diameter of the threads 52 in the barrel member 40. In accordance with another embodiment of the invention, the outer surface of the plunger member 70 includes threads 82 (FIG. 6) that mate with the threads 52 in the barrel member 40. In this embodiment, the plunger member 70 includes gear teeth (not shown) that engage the teeth 32 on the lever 30 so that the plunger member is caused to rotate by movement of the lever. Alternatively, a rotating connection 84 can be used to transmit axial movement of the plunger member 70 by the lever 30 into rotation. It should be understood that instead of the lever 30, other suitable means for rotating the plunger member 70 could be utilized, and that rotation of the plunger member could either be manual or motorized.

To use the apparatus 10 to deposit harvested bone graft material and/or a bone substitute material into a site such as an intervertebral disc space, the bone graft material is placed into the funnel section 54 of the barrel member 40 and then manually pushed toward the second end portion 48 with a loading tool 90 (FIG. 7). The funnel section 54 is then screwed onto the handle assembly 20.

Next, the plunger member 70 is pushed through the passage 23 in the base member 22 until the teeth 80 engage the teeth 32 on the lever 30. The plunger member 70 is now advanced toward the second end portion 48 of the barrel member 40 by pivoting (squeezing) the lever 30. As the plunger member 70 advances toward the position shown in FIG. 2, the bone graft material is smooth advanced along a helical path formed between the threads 52 and the outer surface of the plunger member 70. This helical pathway provides sufficient clearance for bone particles in the bone graft material to be moved without becoming jammed or lodged in the barrel member 70. Continued advancement of the plunger member 70 through movement of the lever 30 forces the bone graft material out of the barrel member 40 through the exit port 62 in a controlled and automated manner.

If the threaded plunger member 70 of FIG. 6 is used, movement of the lever 30 (or any other suitable means) causes the plunger member to rotate and move along the mated threads 52 and 82 toward the second end portion 48. The engagement of the threads 52 and 82 prevents bone particles from getting jammed between the barrel member 40 and the plunger member 70 and forces bone graft material positioned in front of the second end 78 of the plunger member 70 toward the second end portion 48 of the barrel member 40. As with the first embodiment, continued advancement of the plunger member 70 through movement of the lever 30 forces the bone graft material out of the barrel member 40 through the exit port 62 in a controlled and automated manner.

It should be understood by those of ordinary skill in the art that the apparatus described above could either be made from polymeric materials and thus disposable or, alternatively, made from a sterilizable metallic material and thus reusable.

From the above description of the invention, those skilled in the art will perceive improvements, changes and modifications. For example, it should be understood that the apparatus disclosed herein could be used to deposit other materials into the body, and used to deposit bone graft material into bodily locations other than the spine. Such improvements, changes and modifications within the skill of the art are intended to be covered by the appended claims.

Having described the invention, I claim:

1. An apparatus for depositing bone graft material into a mammalian body comprises:
    a barrel member having an inner surface with internal threads, the barrel including an exit port through which bone graft material placed into the barrel exits the barrel;
    a plunger member disposed coaxially within the barrel member for pushing the bone graft material toward the exit port in the barrel, wherein the plunger member is rotatable and includes external threads that are complimentary to and engaged with the internal threads in the barrel member to assist in moving the bone graft material toward the exit port in the barrel; and
    a pivotable lever for advancing the plunger member within the barrel member.

2. The apparatus of claim 1 wherein the plunger member has a smooth outer surface and a helical pathway is defined between the outer surface and the internal threads in the barrel member, whereby the bone graft material is guided through the barrel to the exit port along the helical pathway.

3. The apparatus of claim 1 wherein the outer surface of the plunger member has an outer diameter that is slightly less than the major diameter of the internal threads in the barrel member to help prevent bone graft material from becoming jammed between the outer surface and the internal threads.

4. The apparatus of claim 1 wherein the lever includes a row of rack teeth engaged with a complimentary set of rack teeth on the plunger member, wherein pivotal movement of the lever causes axial movement of the plunger member.

5. The apparatus of claim 1 wherein the exit port is radially oriented.

* * * * *